(12) United States Patent
Lockhart

(10) Patent No.: US 8,618,485 B1
(45) Date of Patent: Dec. 31, 2013

(54) DETECTION OF DISCONTINUITY DENSITIES IN COMPOSITE MATERIALS

(75) Inventor: Patric K. Lockhart, Middletown, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 93 days.

(21) Appl. No.: 13/242,441

(22) Filed: Sep. 23, 2011

(51) Int. Cl.
*G01J 5/02* (2006.01)

(52) U.S. Cl.
USPC .................................................. 250/341.1

(58) Field of Classification Search
USPC ...................................................... 250/341.1
See application file for complete search history.

(56) References Cited

U.S. PATENT DOCUMENTS

2007/0235658 A1* 10/2007 Zimdars et al. .......... 250/390.07
2008/0180111 A1* 7/2008 Federici et al. ................ 324/639

FOREIGN PATENT DOCUMENTS

JP           2002277393 A  *  9/2002   ............. G01N 21/35

* cited by examiner

*Primary Examiner* — David Porta
*Assistant Examiner* — Edwin Gunberg
(74) *Attorney, Agent, or Firm* — James M. Kasischke; Michael P. Stanley

(57) ABSTRACT

A method for detecting suspended discontinuity densities in a material is provided. The method includes transmitting terahertz electromagnetic radiation toward a surface of the material. This radiation is received at an expected location after interacting with the material. The power level of the received radiation is measured and deviation from the expected value is used to determine a suspended discontinuity density gradient in the material. The method can be used with either reflected radiation or transmitted radiation. Embodiments of the method can calculate the index of refraction in the material and correlate this with the suspended discontinuity density of the material.

9 Claims, 3 Drawing Sheets

DETECTION OF DISCONTINUITY DENSITIES IN COMPOSITE MATERIALS

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

BACKGROUND OF THE INVENTION (1) Field of the Invention

The present invention is directed generally towards a non-destructive method for detecting densities of components of a composite material (referred to herein as discontinuity densities and suspended discontinuity densities). More specifically it is directed toward determining micro-inclusion gradients and micro-inclusion gradient boundaries in micro-inclusion-impregnated materials utilizing sub-centimeter wavelength electromagnetic radiation. This method also detects micro-inclusion concentration levels in micro-inclusion-impregnated materials in a nondestructive, contactless fashion.

(2) Description of the Prior Art

Terahertz Time-Domain Spectroscopy (THz-TDS) was first developed in research institutions in the early 1990's. The technology began to see first commercial development later that decade with very large (the size of a refrigerator), very expensive apparatuses for niche research application. Over the following decade, THz-TDS systems became much smaller and operated with much greater dynamic range. For example, the current state of the art system is roughly the size of a suitcase and can image across a bandwidth of 0.03 to 3.5+THz (corresponding to a free space wavelength of about 1 cm to about 100 microns) with a dynamic range of about 100 dB.

Terahertz (THz) imaging combines aspects of optics, such as high resolution imaging, and radio-frequency electromagnetics to yield an imaging technology that can take sub-millimeter resolution pictures of objects hidden within and on the other side of materials. THz waves may not pass through all materials equally well; however, differences in material transparency allow for identification of one material hidden behind another, much like an electromagnetic version of ultrasound.

THz scanners are finding wider usage outside the research community. NASA has employed THz-TDS scanners to detect defects within the tiles on the outside of the Space Shuttle fuel tank. The Transportation Safety Administration (TSA) has employed THz scanners at airport security checkpoints nation-wide to detect concealed objects on people attempting to board planes.

Micro-inclusions are microscopic chunks of material manufactured for a wide variety of uses in research, medicine, consumer goods and various industries. Micro-inclusions are usually between 10 to 300 micrometers in diameter. They are used as lightweight filler in composite materials such as lightweight concrete. Micro-inclusions can impart the following qualities reduced weight, reduced thermal conductivity, and increased resistance to compressive stress that far exceeds that of other similar materials. These properties are exploited in high pressure environments where other similar materials would implode. Micro-inclusions having internal hollows create materials having different properties.

A material for testing can have a desired concentration of micro-inclusions. In making this material, a liquid (uncured) version of the material is put into a curing mold after being mixed with sufficient micro-inclusions to achieve the desired concentration. The buoyancy of the micro-inclusions in the curing liquid causes them to migrate towards the surface of the liquid opposite the pull of gravity while the material/micro-inclusion mixture cures. In other words, the liquid is denser than the micro-inclusions causing the liquid to sink while pushing the micro-inclusions closer to the upper surface. Thus, when the mixture is finished curing, there is a region in the resulting composite material at the lowest point of the material referenced to gravity where most of the micro-inclusions have floated away, and there is a region at the highest point of the material referenced to gravity having an excess of micro-inclusions. Naturally, there is a gradient in the micro-inclusion concentrations at the boundaries where the micro-inclusion concentration shifts due to the aforementioned gravitational/buoyancy effect. As a matter of quality control, it is desirable to maintain these concentrations within the desired limits.

SUMMARY OF THE INVENTION

Accordingly it is an object of the present invention to provide non-destructive method for measuring elements of a composite material having differing distributions.

A further object is determining micro-inclusion densities in a composite material having micro-inclusions.

There is provided a method for detecting suspended discontinuity densities in a material. The method includes transmitting terahertz electromagnetic radiation toward a surface of the material. This radiation is received at an expected location after interacting with the material. The power level of the received radiation is measured and deviation from the expected value is used to determine a density gradient in the material. The method can be used with either reflected radiation or transmitted radiation. Embodiments of the method can calculate the index of refraction in the material and correlate this with the micro-inclusion density of the material.

Other objects and advantages of the present invention will become apparent from the following description, drawings and claims.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein like reference numerals and symbols designate identical or corresponding parts throughout the several views and wherein.

DETAILED DESCRIPTION OF THE INVENTION

FIGS. 1-4 show embodiments of the invention with reference to a test sample 10. Reference numbers for the test sample are the same throughout. Test sample 10 is shown in cross-section. It includes a substrate 12 having micro-inclusions 14 suspended therein. Test sample 10, substrate, and micro-inclusions 14 are not shown to scale. In actual use, micro-inclusions 14 will be much smaller and present at a much greater concentration. Region 16 of sample 10 has a micro-inclusion gradient having many more micro-inclusions 14 at a surface 18 of the sample 10. While application of this technology is particularly applicable to micro-inclusions dispersed in a polymer matrix, it is equally applicable to any group of material agglomerates in suspension in a bulk material where the agglomerates are intended to be arranged with a certain uniformity, absence of uniformity, or gradient.

Figure 1:
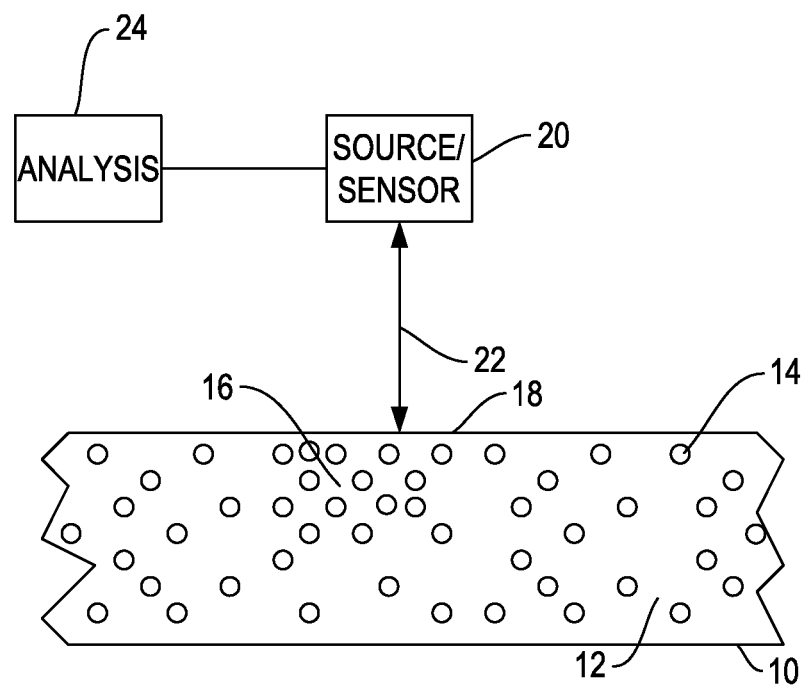
FIG. 1 is a diagram of first embodiment of the invention having a colocated source and sensor for a reflection terahertz radiation system.
Figure 2:
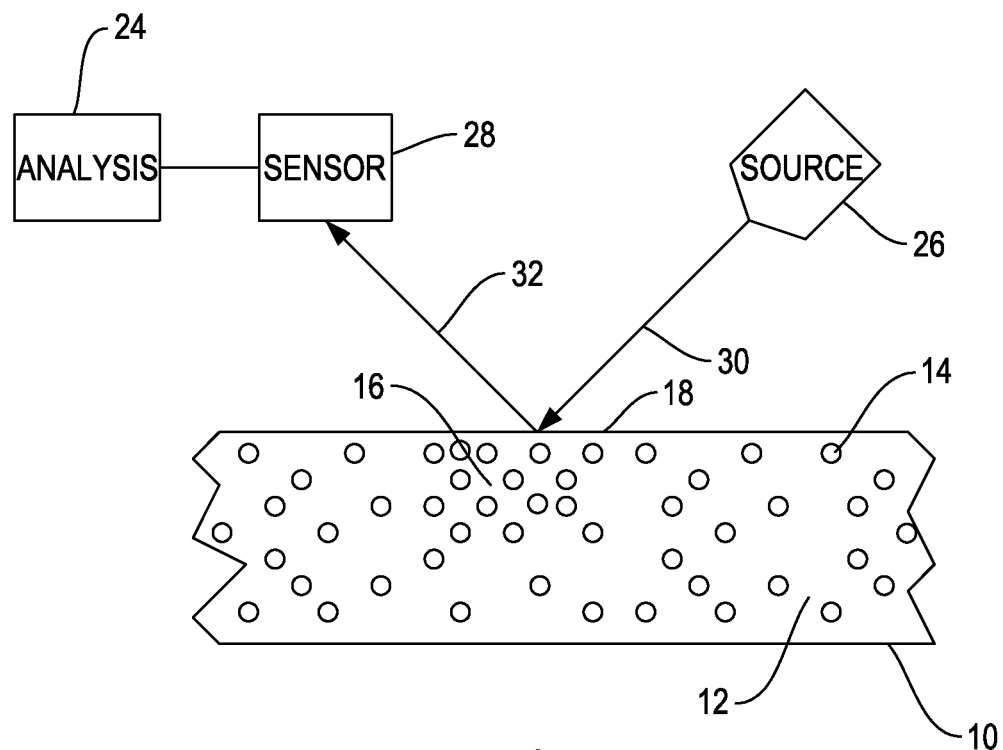
FIG. 2 is a diagram of second embodiment of the invention having an offset source and sensor for a reflection terahertz radiation system.
Figure 3:
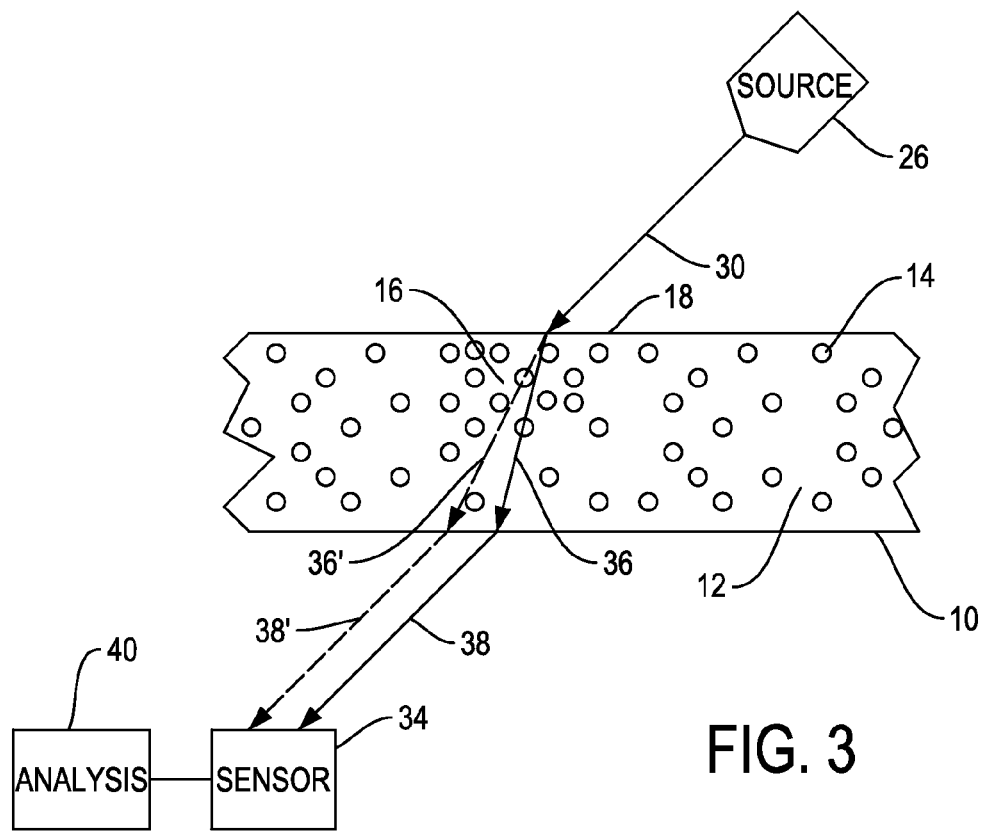
FIG. 3 is a diagram of third embodiment of the invention having an offset source and sensor for a transmission terahertz radiation system.
Figure 4:
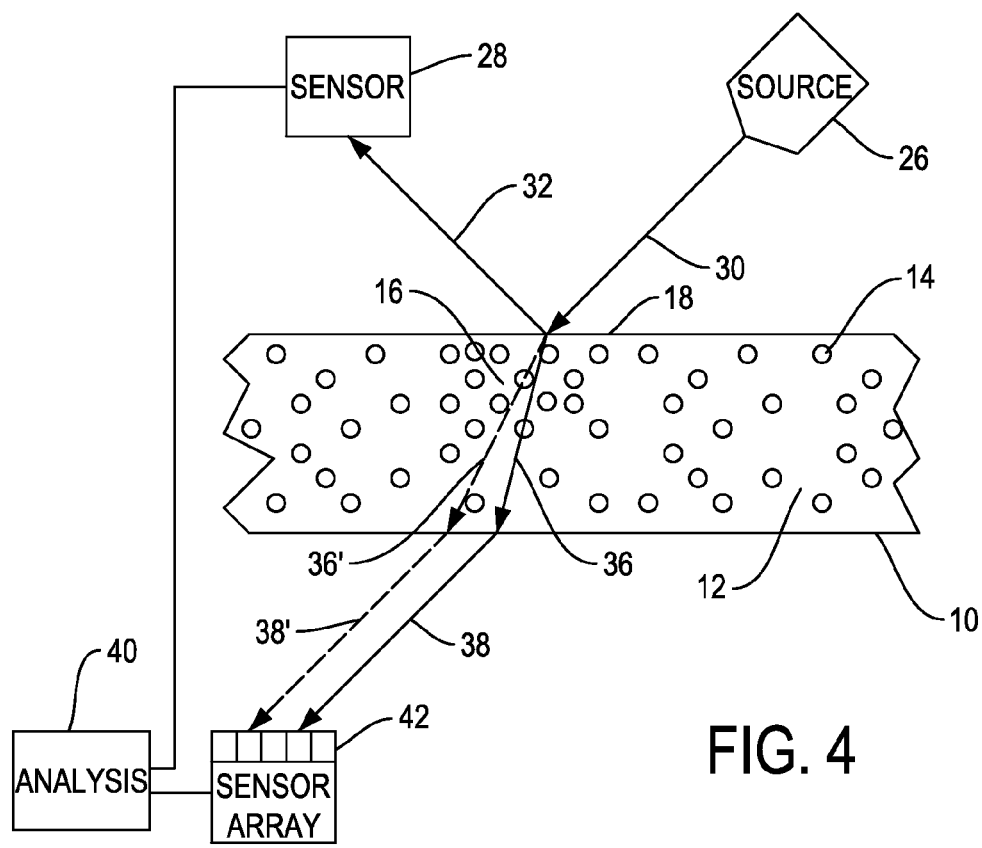
FIG. 4 is a diagram of third embodiment of the invention having an offset source and sensor for a transmission and reflection terahertz radiation system.

A gradient in micro-inclusion concentration can be detected by its effect on electromagnetic waves reflecting from a material surface having a gradient or traveling through a gradient in the material if the gradient in micro-inclusion concentration also causes a gradient in refractive index of the resulting composite material. FIG. 1 shows an embodiment using a surface-normal reflection of electromagnetic waves. FIG. 2 shows an embodiment using an offset reflection of electromagnetic waves. FIG. 3 shows an embodiment using refraction of transmitted electromagnetic waves to determine material characteristics. FIG. 4 shows an embodiment of the invention using both transmitted and reflected electromagnetic waves.

The embodiment shown in FIG. 1 includes a combined electromagnetic radiation source and sensor 20 capable of transmitting electromagnetic radiation shown at 22. Radiation 22 contacts surface 18 of sample 10 and reflects directly back to combined source and sensor 20 along the same path 22. An analysis system 24 is joined to combined source and sensor 20.

In operation, source 20 transmits electromagnetic radiation 22, preferably in the frequency range of about 0.03 to 3.5 THz. The radiation transmission can be a pulse of radiation having a duration assuring reception at source/sensor 20. Radiation 22 contacts surface 18 of sample 10 and is reflected. Reflected radiation along path 22 is received at source/sensor 20. Analysis system 24 monitors the intensity of the received signal. This embodiment allows easy monitoring of reflected signal changes. These changes indicate a refractive index change if no other sources of reflected signal variation (i.e.—surface roughness) are present.

FIG. 2 shows an embodiment having an offset source 26 and reflected radiation sensor 28. This type of arrangement is known in the art as "pitch-catch." Reflected radiation sensor 28 is positioned to receive reflections according to Snell's law. Source 26 transmits electromagnetic radiation along path 30. Electromagnetic radiation 30 reflects from surface 18 of the sample 10, and the reflected radiation follows path 32. Reflected radiation is received at sensor 28. As before, sensor 28 is joined to an analysis system 24. Analysis system 24 monitors the intensity of the received signal to indicate a refractive index change if no other sources of reflected signal variation (i.e.,—surface roughness) are present.

FIG. 3 shows an embodiment having an offset source 26 with a transmitted radiation sensor 34 located on the opposite side of sample 10. Sensor 34 is positioned at an expected transmission location to receive transmitted electromagnetic radiation according to predicted refraction characteristics of sample 10. As before, source 26 provides electromagnetic radiation along path 30. At surface 18, electromagnetic radiation 30 is refracted along path 36. Refracted electromagnetic radiation 36 exits sample 10 and is refracted along path 38 as transmitted electromagnetic radiation. (If a micro-inclusion concentration gradient exists in the material path 36 may be a curved path.) Dashed path 36' shows the expected path of the refracted radiation in the absence of a micro-inclusion gradient. Dashed path 38' shows the expected path of the transmitted electromagnetic radiation in the absence of a micro-inclusion gradient. Sensor 34 is joined to an analysis system 40 for analyzing the transmitted radiation.

In one embodiment, transmitted radiation sensor 34 can be a single sensor positioned such that a lower intensity or an absence of received radiation indicates a material defect. In a more sophisticated embodiment, transmitted radiation sensor 34 can be an array of sensors having each sensor positioned at a different position with respect to the back surface of sample 10. This transmitted radiation sensor array can provide a transmitted radiation reception location to the analysis system. The analysis system can then use this information to calculate the refracted angle and determine various micro-inclusion properties such as the volume micro-inclusion concentration gradient rate of change.

The embodiment shown in FIG. 4 includes analysis of both reflected electromagnetic radiation and transmitted electromagnetic radiation. Source 26 transmits electromagnetic radiation along path 30. A portion of electromagnetic radiation 30 reflects from surface 18 of the sample 10, and the reflected radiation follows path 32. Reflected radiation sensor 28 is positioned to receive reflections according to Snell's law. Reflected radiation sensor 28 is joined to analysis system 40. Analysis system 40 monitors the intensity of the received signal to indicate a refractive index change if no other sources of reflected signal variation (i.e.,—surface roughness) are present. Another portion of electromagnetic radiation on path 30 is refracted into the sample 10 on path 36. Refracted electromagnetic radiation 36 exits sample 10 and is refracted along path 38 as transmitted electromagnetic radiation. Dashed path 36' shows the expected path of the refracted radiation in the absence of a micro-inclusion gradient. A transmitted radiation sensor 34 or sensor array 42 is provided to receive the transmitted radiation 38. Sensor array 42 is joined to analysis system 40 for analyzing the position and intensity of the transmitted radiation. In yet another adaptation of this embodiment, source 26 and sensor 28 could be positioned perpendicular to surface 18, and sensor 34 or sensor array 42 could be perpendicular to the opposite surface of sample 10.

Figure 5A:
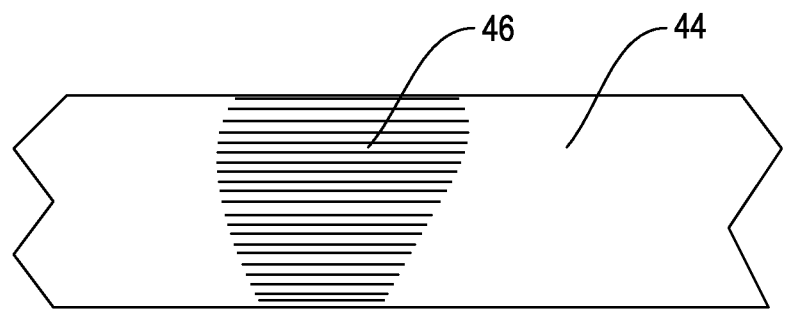
FIG. 5A is a diagram showing an image of a sample taken with a transmission terahertz radiation system.

FIG. 5A shows a representation of transmitted electromagnetic energy 38 received by transmitted radiation sensor 34. In regions having constant concentration of micro-inclusions, electromagnetic radiation is transmitted in the expected manner such as indicated by 44. In regions having a micro-inclusion gradient such as that shown at 16 of FIG. 1, electromagnetic radiation is transmitted to the expected location on sensor 34 or sensor array 42 with a reduced intensity as shown at 46.

Figure 5B:
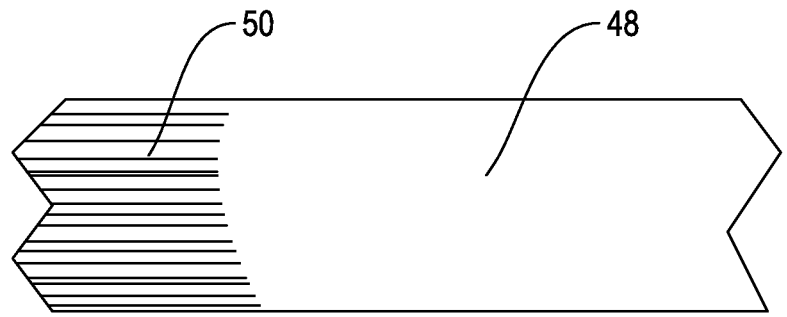
FIG. 5B is a diagram showing an image of a sample taken with a reflection terahertz radiation system.

FIG. 5B shows a representation of reflected electromagnetic radiation 32 received by reflected electromagnetic radiation sensor 28. Regions having a higher or lower concentration of micro-inclusions at the surface 18 of sample 10 have different refractive indices. This results in a comparatively different amount of radiation being reflected from the surface. A surface having a uniform distribution of micro-inclusions is shown at 48, and a surface having a different, uniform concentration of micro-inclusions is shown at 50. A concentration gradient of micro-inclusions exists at the boundary between regions 48 and 50.

The concentration of micro-inclusions in a composite material will affect the effective refractive index of the material directly proportionally to the weighted percentage of the volume ratio between micro-inclusions and material across the imaged material surface or volume. If the refractive index of the micro-inclusions 14 is higher than the refractive index of the bulk material 12 they are suspended in, then the refractive index of the composite material will increase. If the refractive index of the micro-inclusions 14 is lower than the refractive index of the bulk material 12 they are suspended in, then the refractive index of the composite material will decrease. Electromagnetic reflection from a surface increases with the disparity of the refractive indices of the materials comprising the two sides of an interface. For a constant material on one side of the surface (e.g., air) and a varying refractive index material on the other side of the surface (e.g., a material with a varying micro-inclusion gradient), the reflected electromagnetic signal magnitude will be greater from the regions of the material surface where the refractive index is higher.

The surface reflection of electromagnetic radiation in the 100 micron to 1 cm wavelength range will also show the location, magnitude, and boundaries of the micro-inclusion gradient as a change in magnitude of the surface reflection of the electromagnetic radiation in accordance with Snell's Law. The reflection will show greater reflected signal energy from the material surface in the region of the material where the micro-inclusion concentration causes a greater disparity between the material's refractive index and the refractive index of the medium in direct contact with the material surface. As the micro-inclusion concentration causes the composite material's refractive index to become more similar to that of the surrounding media, the surface reflection will decrease. This effect allows examining of large material volumes from a surface analysis if the cured composite material is homogenous along one axis perpendicular to the direction of micro-inclusion buoyancy drift.

The change with micro-inclusion concentration in refractive index and absorption coefficient across the sub-centimeter wavelength range allows calculation of the micro-inclusion concentration in the material. As the micro-inclusion concentration in a material increases, the refractive index and absorption coefficient in the material will decrease (increase) if the micro-inclusions have a lower (higher) attenuation coefficient and absorption coefficient than the matrix material in the micro-inclusion composite material. Parenthetical statements in this paragraph are meant to show that the converse statement is also true. As the volume-percentage of the micro-inclusions increases, the percentage of the material having a lower (higher) refractive index and lower (higher) attenuation coefficient increases and the overall attenuation through the material and reflection coefficient at the surface of the material decreases (increases). Thus, the micro-inclusion concentration can be determined by the attenuation of the electromagnetic radiation through the material. Micro-inclusion concentration at the surface of a composite material can be determined by the magnitude of the reflected electromagnetic radiation from the material's surface.

This imaging method will allow imaging of the micro-inclusion gradient which occurs in the gravitational top and bottom volume of micro-inclusion impregnated materials due to gravitational drift of the micro-inclusions during the curing process. The detection of this micro-inclusion gradient edge will allow manufacturers of micro-inclusion-impregnated materials to accurately determine where the dividing line exists between the gravity-induced micro-inclusion gradient and the regions where the micro-inclusion concentrations are constant. The regions of the material with constant levels of micro-inclusions are useful for applications such as those described in [0007], whereas the regions with variable concentrations of micro-inclusions will not provide the expected application performance response if consistent micro-inclusion concentrations are expected in design. Regions of non-homogeneous micro-inclusion concentrations in acoustic materials will not perform as desired, and this method allows non-destructive inspection to determine such non-homogeneity without exposure to an acoustic environment or as a supplemental diagnostic tool.

This imaging method also allows for determination of micro-inclusion concentration levels in micro-inclusion impregnated materials in a contactless, nondestructive way.

The foregoing description of the preferred embodiments of the invention has been presented for purposes of illustration and description only. It is not intended to be exhaustive nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A method for detecting dispersion of agglomerates in a material comprising:
   transmitting terahertz frequency electromagnetic radiation toward positions on a surface of the material;
   determining an expected reception location for the transmitted radiation after interaction with the material based on the laws of reflection and refraction;
   determining an expected reception intensity for the transmitted radiation after interaction with the material;
   receiving the terahertz electromagnetic radiation after the terahertz electromagnetic radiation has interacted with the material at the expected reception location;
   detecting an intensity of the received radiation at positions on the surface of the material;
   determining a refractive index gradient from the detected intensities; and
   providing an indication of agglomerate dispersion in the material if a refractive index gradient exists.

2. The method of claim 1 wherein:
   transmitting is performed on a first side of the material; and
   receiving is performed on a second, opposite side of the material such that terahertz electromagnetic radiation is transmitted through the material.

3. The method of claim 1 wherein:
   transmitting is performed on a first side of the material; and
   reception is performed on the first side of the material, such that received radiation is reflected from the material.

4. The method of claim 3 wherein incident radiation is incident perpendicularly toward a surface of the material and reception occurs along substantially the same path as transmission.

5. The method of claim 1 wherein:
   said material is a substrate and said agglomerates are a plurality of micro-inclusions suspended therein; and said step of providing an indication of agglomerate dispersion comprises determining a density gradient of micro-inclusions in the substrate.

6. The method of claim 1 wherein said step of determining an expected reception intensity comprises establishing the expected reception intensity based on other regions of the material.

7. A method for detecting dispersion of agglomerates in a material comprising:
  transmitting terahertz electromagnetic radiation toward positions on a first surface of the material;
  determining a first expected reception location for each position on the first surface for transmitted terahertz electromagnetic radiation based on the laws of refraction;
  determining a second expected reception location for each position on the first surface for reflected terahertz electromagnetic radiation based on the laws of reflection;
  determining a first expected reception intensity for transmission of terahertz electromagnetic radiation through the material;
  determining a second expected reception intensity for reflection of terahertz electromagnetic radiation from the material;
  receiving the terahertz electromagnetic radiation at the first expected reception locations on a second opposite side of the material such that terahertz electromagnetic radiation is transmitted through the material;
  receiving the terahertz electromagnetic radiation at the second expected reception locations on the first side of the material such that terahertz electromagnetic radiation is reflected from the material;
  detecting an intensity of the received terahertz electromagnetic radiation at the first expected terahertz reception locations;
  detecting an intensity of the received terahertz electromagnetic radiation at the second expected terahertz reception locations; and
  determining a refractive index gradient across positions on the material from the detected intensities at the first expected terahertz reception locations and the second expected terahertz reception locations;
  providing an indication of agglomerate dispersion in the material based on the determined refractive index gradient.

8. The method of claim 7 wherein:
  said material is a substrate and said agglomerates are a plurality of micro-inclusions suspended therein; and
  said step of providing an indication of agglomerate dispersion comprises determining a density gradient of micro-inclusions in the substrate.

9. The method of claim 7 wherein said step of determining a first expected reception intensity comprises establishing the first expected reception intensity based on other regions of the material.

* * * * *